United States Patent [19]
Lane et al.

[11] Patent Number: 4,734,964
[45] Date of Patent: Apr. 5, 1988

[54] APPARATUS FOR REFURBISHING ACOUSTIC MEMBERS

[75] Inventors: Sanford Lane, Freemont, Calif.; Alan Broadwin, Brooklyn; W. William Podszus, New Rochelle, both of N.Y.

[73] Assignee: Cooper LaserSonics, Inc., Santa Clara, Calif.

[21] Appl. No.: 790,983

[22] Filed: Oct. 24, 1985

[51] Int. Cl.⁴ .............................................. B23P 7/00
[52] U.S. Cl. ..................... 29/33 R; 15/256.5; 29/594; 51/59 SS
[58] Field of Search .......... 29/33 R, 34 R, 50, 602 A, 29/609.1, 402.04, 594; 51/59 SS, 170 R, 241 VS; 15/210 R, 104.09, 104.16, 256.5; 128/24 A

[56] References Cited

U.S. PATENT DOCUMENTS

| | | | |
|---|---|---|---|
| 2,680,333 | 6/1954 | Calosi | 51/59 SS |
| 2,748,298 | 5/1956 | Calosi et al. | 128/24 A X |
| 2,774,193 | 12/1956 | Thatcher | 51/59 |
| 2,802,319 | 8/1957 | Hume | 51/241 |
| 2,990,616 | 7/1961 | Balamuth | 32/26 |
| 3,229,425 | 1/1966 | Homeyer | 51/211 |
| 3,728,828 | 4/1973 | Freedman | 51/204 |
| 3,809,977 | 5/1974 | Balamuth | 318/116 |
| 4,001,982 | 1/1977 | Griffin | 51/211 R |
| 4,014,063 | 3/1977 | Bunke | 15/111 |
| 4,471,824 | 9/1984 | Zownir | 144/330 |

FOREIGN PATENT DOCUMENTS

| | | | |
|---|---|---|---|
| 161748 | 11/1985 | European Pat. Off. | 51/59 SS |
| 220547 | 4/1985 | German Democratic Rep. | 51/59 SS |
| 191760 | 9/1985 | Japan | 51/59 SS |

Primary Examiner—William R. Briggs
Attorney, Agent, or Firm—Vorys, Sater, Seymour and Pease

[57] ABSTRACT

The invention relates to a method and apparatus for cleaning and refurbishing the adjacent planar surfaces of a pair of interchangeable surgical acoustic members. The device includes a spaced pair of outwardly biased abrasive members mounted on a rotatable housing so that the tool can be located between the adjacent planar faces and about a threaded connection between them. Rotation of the device causes the abrasive members in contact with the opposed planar surfaces to clean and refurbish those surfaces. The method of using the device is also disclosed. The device is provided as a component of a maintenance kit for the acoustic members. The kit also includes a wire brush for cleaning the threaded joint, non-shredding swabs for wiping the threads and acoustic joint, and a brush for cleaning the bores of the acoustic member.

25 Claims, 2 Drawing Sheets

APPARATUS FOR REFURBISHING ACOUSTIC MEMBERS

BACKGROUND OF THE INVENTION

This invention relates to a method and apparatus for cleaning and refurbishing interchangeable surgical acoustic members. More particularly, this invention relates to a rotatable member structurally adapted to fit between two adjacent threaded members and having oppositely mounted abrasive film discs for cleaning and refurbishing the opposed faces of coupled members by rotation of the device. Still more particularly, this invention relates to a method for cleaning and refurbishing the opposed contact faces of an adjacent pair of coupling members by providing a pair of oppositely mounted abrasive film disc on a hollow carrier secured by a resilient member to provide adequate abrasive pressure simultaneously against the opposed acoustic surfaces.

Surgical instruments are known to the art which utilize replaceable or interchangeable acoustic members threadedly secured through an acoustic interface to a handpiece to comprise an ultrasonically vibrating member useful in performing surgical procedures of various types. Such devices are unlike the vibrating elements of some dental devices which are brazed and thus have a permanently controlled acoustic interface and are also unlike the threaded joint interface of some industrial ultrasonic devices which are torqued together by skilled mechanics and remain in place for long periods of time. In contrast to those applications of ultrasonic vibrations, replaceable or interchangeable acoustic members in hand-held surgical instruments present the unique problem in that the vibrating members of a surgical ultrasonic device are mixed, matched, replaced, and interchanged after each surgical use. In practice, such an exchange is usually accomplished by non-technical operating room personnel.

Experience with such instruments has taught that the mating surfaces which transmit the acoustic energy from a handpiece to an acoustic member through an acoustic interface must be clean, flat, and smooth in order to achieve a maximum energy transfer with a minimum of mechanical losses, thus to insure consistent performance over the life of the acoustic members. While the acoustic members supplied are always clean, flat and smooth when initially delivered, repetitive use of previously-used acoustic members, which have not been renewed and inspected at the source of manufacture, has sometimes caused a degradation in performance and, in some instances, a fracture or failure of the acoustic member.

A degradation in performance caused by a less than optimum acoustic interface between two coupled members is particularly troublesome because it does not necessarily result in an immediate catastrophic failure of the surgical system. Rather, an imperfect coupling usually causes the reduction in mechanical and surgical efficacy in a first phase, folowed subsequently by a failure of the elements. Clearly, a decreased ability to fragment firm tumor is undesirable since such ultrasonic surgical equipment is often used in cases considered inoperable by other means. Accordingly, it is clear that a failure of the acoustic members is expensive from both the social and business points of view.

In the art, a cleaning strip has been provided with a reusable tip to allow cleaning of the face of a handpiece connecting body. That cleaning strip, made from a 12 micron lapping film, is used to clean the acoustic coupling surface of the connecting body only, rather than both surfaces. The performance of that strip, generally used by an unskilled operator, has not been completely satisfactory in that an improper application of the cleaning strip may sometimes upset the flatness of the coupling surfaces.

Accordingly, it is an overall object of this invention to provide an improved means for cleaning and refurbishing the acoustic coupling surfaces of an ultrasonic surgical member.

It is another overall object of the invention to determine an optimum medium for cleaning and resurfacing the acoustic surfaces without degrading their initial machine smooth flat planes.

It is an additional object of this invention to provide an apparatus to mount the abrasive film according to the invention in such a way as to be inexpensive so that the mounting means can be used once and then disposed.

It is still an additional object of this invention to provide such a device for mounting an abrasive for use by unskilled personnel to clean two adjacent mating acoustic surfaces at the same time, without precision holding and fixturing devices.

It is another object of this invention to provide a method and apparatus for refurbishing acoustic surfaces surrounding a male thread as well as a female thread.

It is still another object of this invention to provide such a device as a component in a maintenance kit for surgical acoustic members which also contains brushes and swabs to ensure the surgical performance of the members.

These and other objects will become apparent from a detailed description of the preferred embodiment, taken in conjunction with the drawings.

BRIEF SUMMARY OF THE INVENTION

Directed to achieving the foregoing objects and overcoming the problems in the prior art, an apparatus according to the invention for cleaning and refurbishing of joined acoustic members comprises a generally cup-shaped housing or carrier plate having a base surface with a bore therein terminating in an axially-extending gripping surface, which housing is structurally adapted to be rotated about an axially-extending member provided by an adjacent male threaded surface disposed through the axial bore in the base of the cup. The axially-extending periphery of the housing is preferably knurled to faciliate rotation during coupling. A pair of oppositely mounted abrasive film members, each preferably in the form of an annular disc, are separated by a resilient member, preferably a foam disc, to present abrasive surfaces simultaneously to the acoustic faces of the coupled acoustic members. Preferably, the abrasive comprises a mylar-backed abrasive with a grit of 30 micron ±10 micron as an optimum medium for cleaning and resurfacing the acoustic surfaces without degrading their initial machine smooth flat planes.

In use, the refurbishing tool is positioned between the acoustic surfaces of adjacent acoustic members, the acoustic tip is threaded into the acoustic vibrator so that the tool is captured between the opposing coupling surfaces and the tool is rotated by grasping its carrier housing. In order to free the parts, the direction of rotation of the tool is reversed. The procedure may be repeated until visual inspection of the opposed acoustic surfaces verifies that they are clean and shiny.

The apparatus is preferably provided as a component of a maintenance kit to ensure the continued adequate performance of the surgical members. The kit includes a wire brush for cleaning the threaded joint of the members; non-shredding swabs for removing debris from the threads and acoustic part; and a nylon brush for cleaning the bore of the tip and the extender.

DETAILED DESCRIPTION OF THE PREFERRED EMBODIMENT

Figure 1:
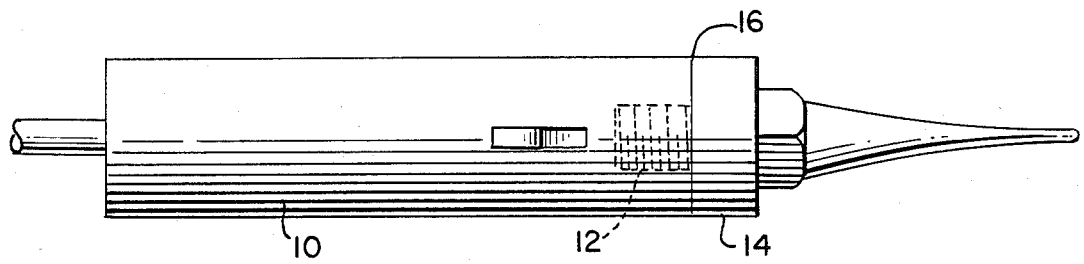
FIG. 1 is a diagram of a representative prior art pair of acoustic member defining an acoustic interface.

In FIG. 1, a first acoustic member 10 is threadedly engaged as at 12 with a second acoustic member 14 to define an acoustic interface 16 at the joinder thereof. The opposed adjacent faces of the members 10 and 14 which define the acoustic interface are flat, smooth, and planar surfaces in order to effectively transmit acoustic energy from the member 10 to the member 14.

Figure 2:
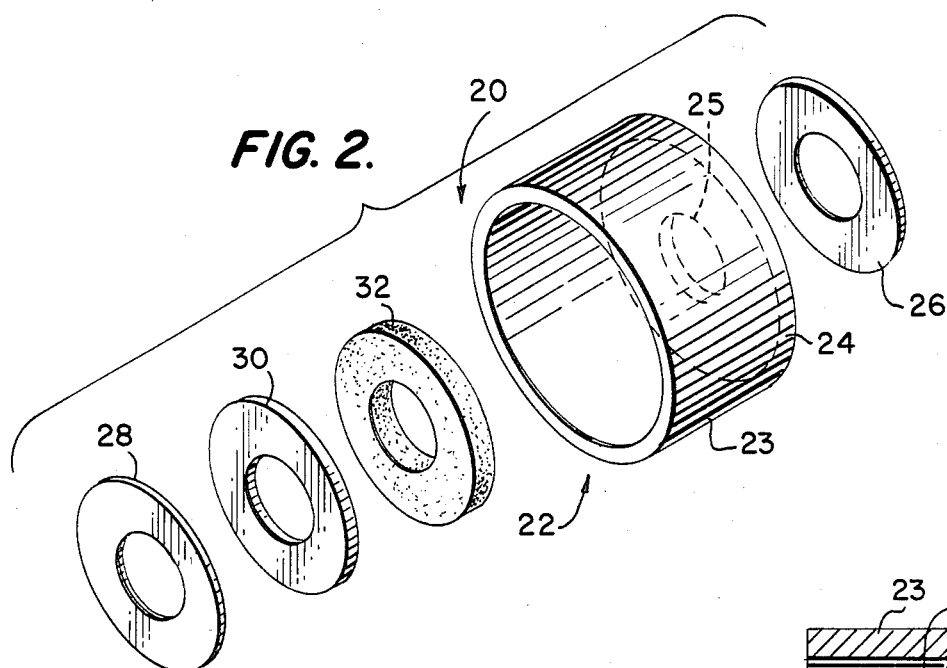
FIG. 2 is a perspective view of the components of the apparatus according to the invention.

FIG. 2 is a perspective illustration of the components of the refurbishing tool 20 according to the invention. The tool carrier comprises a housing 22 which preferably has an axially extending wall portion 23 merging into an annularly-shaped base portion 24 defining an axially central opening 25 therein to permit the male thread of the acoustic member 14 to extend therethrough when in use. A abrasive film disc 26 is secured to the outer surface of the base portion 24. A second abrasive film disc 28 is secured to a disc carrier 30 and positioned axially adjacent to a resilient member 32 to form the structure shown in cross section in FIG. 3.

Preferably, each of the annularly-shaped film discs is made from a mylar-based aluminum oxide lapping film which is commercially available having a grit of 30 microns ±10 micron to provide an optimum medium for cleaning and resurfacing the acoustic surfaces without degrading their initial machine-smooth flat planes.

The disc carrier 30 is preferably made from a material, such as an epoxy sheet, which is sufficiently flat and rigid to support the abrasive film disc. The carrier preferably is approximately ½" in diameter, with an opening sized to accommodate the male threaded member of the acoustic member 14, i.e. about 0.265" in diameter.

The resilient member 32 is also shaped as an annular disc having dimensions approximately those of the adjacent disc carrier 30 and abrasive film discs 26 and 28. The resilient member 32 provides an adequate pressure against the opposed acoustic surfaces of the members 10 and 14 simultaneously. The resilient member is significant to the proper functioning of the refurbishing tool since, in its absence, an operator will be unable to obtain either an adequate pressure on the abrasive of members 26 and 28 against the adjacent acoustic face for cleaning or refurbishing, or would immediately lock the refurbishing tool between the acoustic members before any relative motion was obtained between the abrasive film and the acoustic coupling surfaces so that refurbishing could not be accomplished. Thus, for the abrasive disc of the type described, a suitable foam carrier is in the form of a polyethylene tape having a nominal thickness of about 1/16", commercially provided in the form of a double-sided adhesive with one side paper covered.

Figure 3:
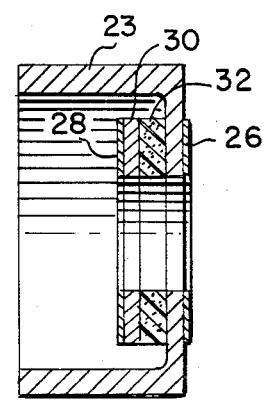
FIG. 3 is a side cross sectional view of the refurbishing tool according to the invention.
Figure 4:
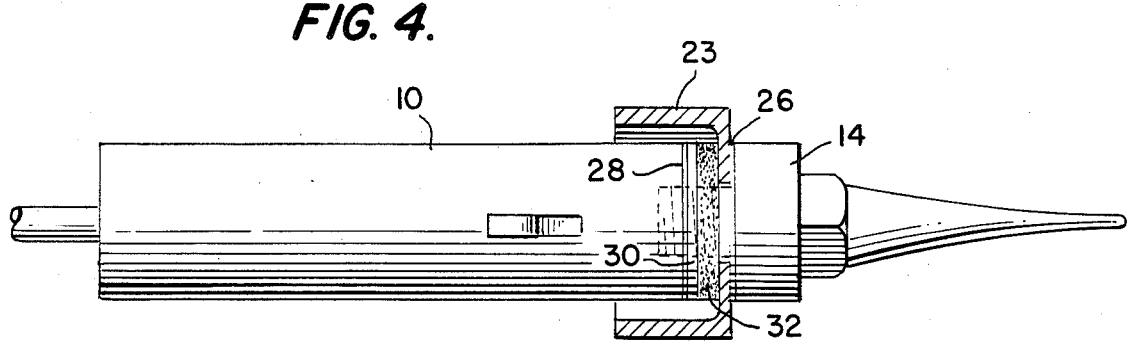
FIG. 4 is a diagrammatic side view of a refurbishing tool according to the invention interposed between a pair of acoustic members as in FIG. 1 to refurbish their adjacent acoustic faces.

In use, as is shown in FIG. 3, starting with a dry acoustic vibrator 10 and a tip 14, the refurbishing tool 20 is axially positioned between the member 10 and the member 14. The member 14, i.e. a tip, is lightly threaded into the member 10 in such a way that the tool 20 is captured between the two opposed coupling surfaces of the members 10 and 14 respectively. The tool 20 is then rotated about the axis until the parts tighten. Thereafter, the direction of rotation of the tool is reversed to free the parts. The foregoing steps are repeated a sufficient number of times so that when the members are unthreaded, a visual check of the surfaces verifies that they are clean and shiny. Thereafter, the refurbished surfaces are wiped with a non-shredding swab, wetted with isopropyl alcohol or hydrogen peroxide to remove any deposited grit.

In a preferred embodiment, the refurbishing tool is provided in kit form together with a brush used to clean the female threads of all joints, non-shredding swabs used for wiping threaded joints of biological or other debris, and a brush used for cleaning out the bore of the various acoustic members so that the correct impedance and matching fluid flow parameters of the system can be maintained for optimum operation.

In the alternative, the resilient member could be replaced by a spring to bias the abrasive member against the adjacent surface during cleaning.

Figure 5:
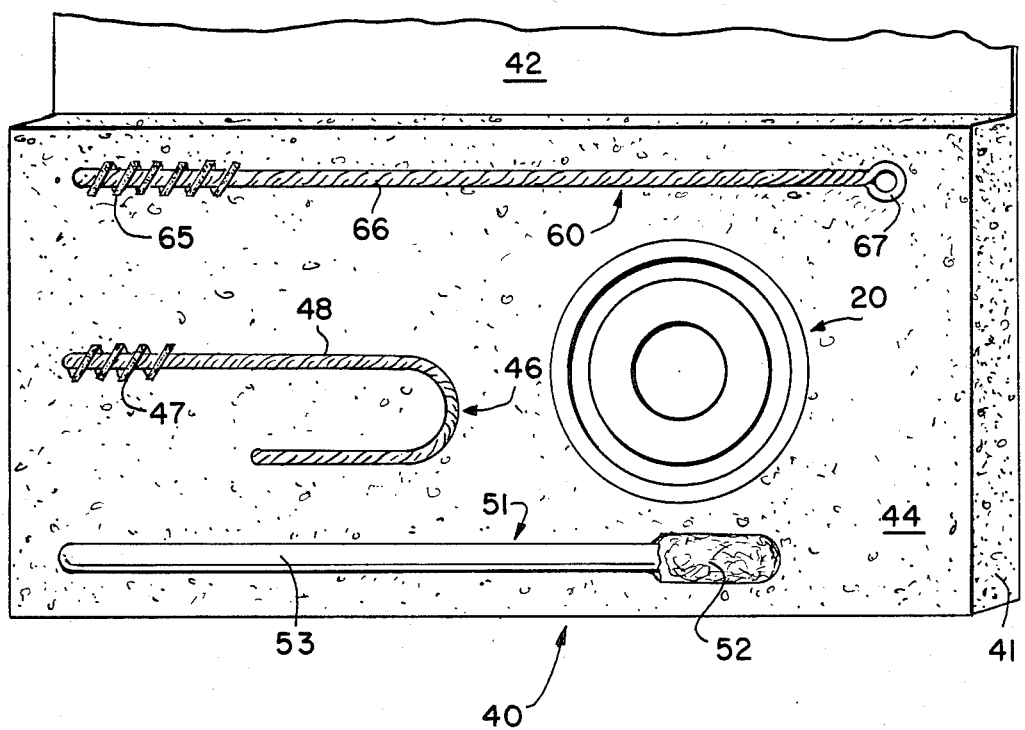
FIG. 5 is a plan view of a maintenance kit in which the refurbishing tool is supplied as a component.

FIG. 5 shows a maintenance kit in which the refurbishing tool, as described in connection with FIGS. 1–4, is provided with additional elements which have been designed or selected for insuring adequate and continuing ultrasonic surgical performance of the mated acoustic members. Thus, a maintenance kit, designated generally by the reference numeral 40 includes a suitable carton-like package 41 and a removable top portion 42. A support member, such as made of a foamed plastic material 44, defines a plurality of contoured locations of predetermined shape to accommodate the various tools.

As described above, the refurbishing tool 20 ensures the quality of the acoustic interface. A wire brush 46 is provided to insure the cleanliness of the threaded joint. Preferably, the wire brush includes a bristle 47 secured to a length of rigid wire 48 formed in a generally U-shape to constitute a thread-cleaning brush. The brush wire is preferably made from stainless steel, as is the stem wire which is preferably twisted in order to form a convenient shape for the user.

The third component of the kit is a non-shredding swab 51, for removing any debris from the threads and the acoustic joint without further contamination. Preferably, the cleaning swab comprises a foam head of a suitable material such as TEX WIPE No. TX 710, secured to a nylon handle 53 and adhered with a non-contaminating epoxy.

The fourth component of the kit includes a nylon brush 60 for insuring the cleanliness of the top and extender bore so that tissue build-up does not effect the operational frequency of the members. The brush includes a nylon bristle tip 65 secured to a length of wire 66 having a suitable rigidity, and forming an eyelet 67 at its distal end for the convenience of the user.

The foregoing combination thus comprises a maintenance kit for an acoustic member which, when provided in combination with the refurbishing tool, is capable of being used in combination to ensure an adequate and continuing ultrasonic surgical performance.

In use, the non-shredding swab 51 is used to wipe the surface of the acoustical member. The swab is preferably wetted with isopropyl alcohol or hydrogen peroxide to remove any deposited grit. In cleaning the acoustic members, the kit of FIG. 5 is important in its ability to attend to all of the coupling surfaces and acoustic member surfaces. Thus, in addition to the refurbishing tool already described for maintaining the main coupling surfaces, the brush 46 is used to clean the female threads of all joints, while the non-shredding swab 51 is used for wiping the threaded surfaces for removing biological or other depris. The brush 60 is used for cleaning out the bore of the various acoustic members so that the correct impedance matching and fluid flow parameters of the system can be maintained for optimum operation of the ultrasonic system.

The refurbishing tool has a number of advantages over the prior art in that it provides an effective but convenient device, usable by unskilled personnel without an undue risk of destroying the flat planar surface condition of adjacent parts of an ultrasonic vibrator. Thus, the tool according to the invention maintains the acoustic coupling surfaces of the ultrasonic surgical member and provides a convenient means for optionally cleaning and polishing the acoustic surfaces of adjacent acoustic members. The tool also provides an inexpensive means for performing the necessary cleaning operation and allows two mating acoustic surfaces to be cleaned at the same time without a precision holding and fixturing device to maintain the quality of the acoustic coupling surfaces. As constructed, the tool can refurbish acoustic surfaces surrounding a male thread as well as a female thread and takes into account the threaded joint of the adjacent acoustical members.

This invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. A device for simultaneously refurbishing the adjacent planar surfaces of a pair of coupled axially-extending members comprising:
   a housing structurally adapted to be axially disposed intermediate the opposed planar surfaces of the adjacent axially-extending members;
   a first abrasive film member secured to said housing in a position to contact one of said pair of opposed planar surfaces;
   a second abrasive film member secured to said housing at a position axially remote from said first abrasive film member to contact the other of said pair of opposed planar surfaces; and
   resilient means located intermediate said first and said second abrasive film members to bias said film members outwardly to contact the planar surfaces of said pair of coupled axially extending members.

2. The device as set forth in claim 1 wherein said resilient means provides sufficient pressure on said first and said second abrasive film members to clean and refurbish the adjacent planar surfaces of said pair of coupled axially-extending members while permitting rotation of the device about its axis so that said film members clean said surfaces while said device is rotating.

3. The device as set forth in claim 1 wherein said resilient means comprises a disc of polyethylene.

4. The device as set forth in claim 1, wherein said resilient member comprises a spring.

5. The device as set forth in claim 1, further comprising a carrier plate to which said first abrasive film member is mounted.

6. The device as set forth in claim 1, wherein said first and said second film members and said resilient means, and at least a portion of said housing, are disc-shaped respectively defining axially-aligned annuli having an opening therein to receive therethrough a male threaded member on one of said pair of said coupled axially-extending members.

7. The device as set forth in claim 1, wherein said housing comprises an axially-extending wall portion merging into an annular base portion, said wall portion being defined at a diameter larger than the diameter of said first and said second abrasive film members and said resilient member.

8. The device as set forth in claim 7, wherein the outer surface of said axially-extending wall portion is knurled to act as a gripping location for rotation of the tool intermediate said pair of coupled axially extending members.

9. The device as set forth in claim 1 in further combination with a kit, said device comprising a component of said kit, said kit further comprising at least one of the following items:
   means structurally adapted for cleaning a threaded joint between said members;
   means structurally adapted for removing debris from either threads of a threaded joint between said members or an acoustic interface between said members; and
   means structurally adapted for cleaning a bore in said members.

10. The device as set forth in claim 9, wherein said means structurally adapted for cleaning a threaded joint between said members comprises a U-shaped wire brush.

11. The device as set forth in claim 9, wherein said means structurally adapted for removing debris from either threads of a thread joint between said members or an acoustic interface between said members comprises non-shredding swabs.

12. The device as set forth in claim 9, wherein said means structurally adapted for cleaning a bore in said members comprises an elongated brush.

13. In combination:
   a first acoustic member defining a first planar acoustic surface;
   a second acoustic member defining a second planar acoustic surface, one of said first and said second acoustic members having a male threaded member for threadedly engaging a mating female threaded opening in the other acoustic member, said first acoustic member and said second acoustic member defining an acoustic interface therebetween when threadedly engaged; and a refurbishing tool located intermediate said first acoustic member and said second acoustic member for simultaneously cleaning the adjacent first and second planar surfaces thereof, said tool comprising means for supporting a spaced pair of outwardly-biased abrasive members, said tool further defining a bore therethrough receiving therethrough the male threaded member of said pair of acoustically coupled members, so that rotation of said tool about an axis while said abrasive film members are in contact with the opposed planar surfaces of said members causes said planar surface to be cleaned and refurbished.

14. The combination as set forth in claim 13, wherein said tool further comprises resilient means located intermediate each of said spaced pair of abrasive members, for outwardly-biasing said abrasive members.

15. The combination as set forth in claim 14, wherein said resilient means provides sufficient pressure on said first and said second abrasive film members to clean and refurbish the adjacent first and second planar surfaces of the coupled first and second acoustic members while permitting rotation of the tool about its axis so that said film members clean said first and second planar surfaces while said tool and said surfaces are relatively rotated.

16. The combination as set forth in claim 15, wherein said resilient means comprises a disc of polyethylene.

17. The combination as set forth in claim 13, wherein said tool further comprises a carrier plate to which said first abrasive film member is mounted.

18. The combination as set forth in claim 13, wherein said tool further comprises resilient means, and wherein said first and said second film members, said resilient means, and at least a portion of said housing are disc-shaped respectively defining axially-aligned annuli having an opening therein to receive therethrough a male threaded member on one of said coupled first and second acoustic members.

19. The combination as set forth in claim 13, wherein said tool comprises a housing which includes an axially-extending wall portion merging into an annular base portion, said wall portion being defined at a diameter larger than the diameter of said first and said second abrasive film members and a resilient member interposed therebetween.

20. The combination as set forth in claim 19, wherein the outer surface of said axially extending wall portion is knurled to act as a gripping location for rotation of the tool intermediate said pair of coupled axially extending members.

21. The combination as set forth in claim 13, wherein said reburshing tool prior to use comprises a component of a maintenance kit for said first and said second acoustic members.

22. The combination as set forth in claim 21 wherein said kit further comprises at least one of the following items:

means structurally adapted for cleaning a threaded joint between said members;

means structurally adapted for removing debris from either threads of a threaded joint between said members or an acoustic interface between said members; and means structurally adapted for cleaning a bore in said members.

23. The combination as set forth in claim 22, wherein said means structurally adapted for cleaning a threaded joint between said members comprises a U-shaped wire brush.

24. The combination as set forth in claim 22, wherein said means structurally adapted for removing debris from either threads of a thread joint between said members or an acoustic interface between said members comprises non-shredding swabs.

25. The combination as set forth in claim 22, wherein said means structurally adapted for cleaning a bore in said members comprises an elongated brush.

* * * * *